(12) United States Patent
Tanoue et al.

(10) Patent No.: US 9,169,238 B2
(45) Date of Patent: Oct. 27, 2015

(54) SOLID PHARMACEUTICAL COMPOSITION

(75) Inventors: Yutaka Tanoue, Osaka (JP); Junya Nomura, Osaka (JP)

(73) Assignee: Takeda Pharmaceutical Company Limited, Osaka (JP)

(*) Notice: Subject to any disclaimer, the term of this patent is extended or adjusted under 35 U.S.C. 154(b) by 211 days.

(21) Appl. No.: 12/737,612

(22) PCT Filed: Jul. 29, 2009

(86) PCT No.: PCT/JP2009/063833
§ 371 (c)(1),
(2), (4) Date: Jan. 28, 2011

(87) PCT Pub. No.: WO2010/013835
PCT Pub. Date: Feb. 4, 2010

(65) Prior Publication Data
US 2011/0123615 A1    May 26, 2011

Related U.S. Application Data

(60) Provisional application No. 61/085,201, filed on Jul. 31, 2008, provisional application No. 61/085,627, filed on Aug. 1, 2008.

(51) Int. Cl.
| | |
|---|---|
| *A61K 31/4245* | (2006.01) |
| *A61K 31/5415* | (2006.01) |
| *A61K 9/20* | (2006.01) |
| *A61P 9/12* | (2006.01) |
| *A61P 9/00* | (2006.01) |
| *A61P 7/10* | (2006.01) |
| *C07D 413/14* | (2006.01) |

(52) U.S. Cl.
CPC .................................. *C07D 413/14* (2013.01)

(58) Field of Classification Search
USPC .......... 424/401, 452, 468, 499; 514/317, 338, 514/561
See application file for complete search history.

(56) References Cited

U.S. PATENT DOCUMENTS

| | | | | |
|---|---|---|---|---|
| 4,444,769 | A * | 4/1984 | Blume et al. ................ | 514/223.5 |
| 5,243,054 | A | 9/1993 | Naka et al. | |
| 5,721,263 | A | 2/1998 | Inada et al. | |
| 5,958,961 | A | 9/1999 | Inada et al. | |
| 6,228,874 | B1 | 5/2001 | Inada et al. | |
| 7,625,940 | B2 | 12/2009 | Solomon | |
| 2001/0004640 | A1 | 6/2001 | Inada et al. | |
| 2001/0011098 | A1 | 8/2001 | Inada et al. | |
| 2003/0068374 | A1 | 4/2003 | Kamei et al. | |
| 2004/0039038 | A1 | 2/2004 | Bernardon et al. | |
| 2004/0147605 | A1 * | 7/2004 | Onuki et al. ................ | 514/561 |
| 2005/0032854 | A1 | 2/2005 | Kawahara et al. | |
| 2006/0159747 | A1 | 7/2006 | Schumacher et al. | |
| 2006/0281795 | A1 | 12/2006 | Kuroita et al. | |
| 2007/0077307 | A1 | 4/2007 | Rosenberg et al. | |
| 2007/0160665 | A1 | 7/2007 | Brand et al. | |
| 2008/0004320 | A1 | 1/2008 | Nakagawa | |
| 2009/0054502 | A1 | 2/2009 | Kuroita et al. | |
| 2009/0208584 | A1 * | 8/2009 | Yoshinari et al. ............ | 424/499 |
| 2010/0016382 | A1 | 1/2010 | Nomura et al. | |
| 2012/0172401 | A1 | 7/2012 | Kuroita et al. | |

FOREIGN PATENT DOCUMENTS

| | | |
|---|---|---|
| EP | 0 628 313 A1 | 12/1994 |
| EP | 1 258 254 A1 | 11/2002 |
| EP | 1 452 176 A1 | 9/2004 |
| EP | 1 787 647 A1 | 5/2007 |
| GE | P 2011 5138 B | 1/2011 |
| GE | P 2012 5420 B | 3/2012 |
| JP | 07-053373 A | 2/1995 |
| JP | 2001-294524 A | 10/2001 |
| WO | WO 02/12210 A1 | 2/2002 |
| WO | WO 2004/028505 A1 | 4/2004 |
| WO | WO 2005/080384 A2 | 9/2005 |
| WO | WO 2006/063737 A1 | 6/2006 |
| WO | WO 2006/124713 A2 | 11/2006 |
| WO | WO 2006/132440 * 12/2006 ............. A61K 47/38 | |
| WO | WO 2008/045006 A1 | 4/2008 |
| WO | WO 2008/068217 A2 | 6/2008 |
| WO | WO 2008/123536 A1 | 10/2008 |
| WO | WO 2009/017812 A2 | 2/2009 |
| WO | WO 2009/058950 A2 | 5/2009 |
| WO | WO 2010/075347 A2 | 7/2010 |

OTHER PUBLICATIONS

Badwy et al., "Microenvironmental pH Modulation in Solid Dosage Forms". Journal of Pharmaceutical Sciences, vol. 96, No. 5, May 2007.*

(Continued)

*Primary Examiner* — Walter Webb
(74) *Attorney, Agent, or Firm* — Foley & Lardner LLP

(57) ABSTRACT

The present invention relates to a solid preparation containing a compound represented by the formula (I) wherein each symbol is as defined in the specification, or a salt thereof, a pH control agent and a diuretic, which is superior in the stability and dissolution property of the compound represented by the formula (I) and the diuretic.

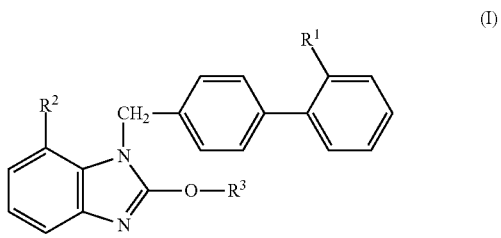

(I)

8 Claims, 1 Drawing Sheet

(56) References Cited

OTHER PUBLICATIONS

Hoyer et al., "Molecular, pharmacological and functional diversity of 5-HT receptors," Pharmacology, Biochemistry and Behavior, 2002, 71:533-554.
WHO Drug Information, 2006, 20(2):59-162.
International Search Report mailed Mar. 18, 2010 in PCT/JP2009/063833, 2 pages.
Franse et al., "Hypokalemia Associated With Diuretic Use and Cardiovascular Events in the Systolic Hypertension in the Elderly Program," Hypertension, 2000, 35:1025-1030.
Scott et al., "Are thiazide diuretics preferred as first-line therapy for hypertension? An appraisal of the Antihypertensive and Lipid-lowering Treatment to Prevent Heart Attack Trial (ALLHAT)," Internal Medicine Journal, 2003, 33:327-330.
Tobian, Louis, M.D., "Perspectives on Treating Hypertension," The American Journal of Medicine, Oct. 31, 1986, 81(Supp 4C):2-7.

* cited by examiner

SOLID PHARMACEUTICAL COMPOSITION

CROSS-REFERENCE TO RELATED APPLICATIONS

This application is a National Stage application of PCT/JP2009-063833, filed Jul. 29, 2009, which claims priority from U.S. Provisional Application Nos. 61/085,201, filed Jul. 31, 2008, and 61/085,627, filed Aug. 1, 2008, the entire contents of which are hereby incorporated by reference.

TECHNICAL FIELD OF THE INVENTION

The present invention relates to a solid preparation comprising a compound represented by the formula (I) to be shown below, a pH control agent and a diuretic, which is superior in the stability and dissolution property of the compound (I) and the diuretic.

BACKGROUND OF THE INVENTION

It is important that pharmaceutical products be effective and safe. Even when a pharmaceutical product is effective and safe immediately after production, if the drug is easily decomposed or denatured during storage and distribution of the pharmaceutical product, it is not considered to be effective and safe as a pharmaceutical product. Therefore, the stability of the drug is extremely important for pharmaceutical products.

To secure effectiveness and safety of a pharmaceutical product, not only the effectiveness and safety of the active ingredient itself are important but also the properties of the pharmaceutical preparation such as the drug dissolution property and the like in the body are extremely important. For example, when the dissolution of the drug from the pharmaceutical preparation is too late, the blood concentration of the drug does not reach an effective level, and the expected efficacy may not be sufficiently exhibited. On the other hand, when the dissolution of the drug from the preparation is too fast, the blood concentration of the drug increases sharply, causing a high risk of side effects.

In other words, pharmaceutical products are required to ensure, in addition to effectiveness and safety, the stability of the drug and a certain level of the drug dissolution property.

The dissolution property of a drug is known to correlate with the solubility thereof. In general, lower solubility of a drug is known to cause slower dissolution property of the drug.

A benzimidazole derivative having a strong angiotensin II receptor antagonistic activity, which is represented by the formula (I)

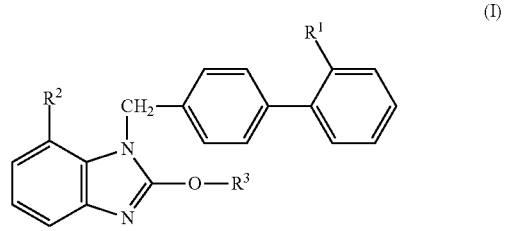

(I)

wherein $R^1$ is a monocyclic nitrogen-containing heterocyclic group having a deprotonizable hydrogen atom, $R^2$ is an esterified carboxyl group and $R^3$ is an optionally substituted lower alkyl, or a salt thereof (hereinafter sometimes to be referred to as compound (I)), particularly (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate salt (patent document 1), is considered to be a promising therapeutic drug for hypertension and the like. However, the properties of a pharmaceutical preparation containing compound (I) need to be controlled to stabilize compound (I) because compound (I) is unstable in the neutral pH range, at which the pharmaceutical preparation is generally produced. Nevertheless, the solubility of compound (I) is low at the pH range where compound (I) is stable. In addition, a combination drug product composed of compound (I) and other active ingredient such as diuretic and the like cannot be easily formulated into a preparation superior in stability and dissolution property since the chemical properties are different.

As a combination drug product, a combination of a compound having an angiotensin II antagonistic activity and a compound having a diuretic action (patent document 2), and an internal solid preparation containing acetaminophen granules obtained by a separating granulation method to suppress the unpleasant taste and prevent discoloration of acetaminophen (patent document 3) are known. However, a combination drug product of compound (I) and a diuretic, which simultaneously affords drug stability and solubility, namely, dissolution property, has not been known.

CITATION LIST

Patent Literature patent document 1: WO2005/080384
patent document 2: U.S. Pat. No. 5,721,263
patent document 3: JP-A-2001-294524

SUMMARY OF THE INVENTION

Problems to be Solved by the Invention

A preparation containing compound (I) and a diuretic is effective for the prophylaxis or treatment of circulatory diseases such as hypertension, cardiac failure, diabetic nephropathy, arteriosclerosis and the like, and has extremely high clinical usefulness.

The problem of the present invention is to provide a solid preparation superior in the stability of compound (I) and a diuretic as well as the dissolution property thereof.

Means of Solving the Problems

The present inventors have conducted intensive studies in an attempt to simultaneously achieve the stability of compound (I) in a preparation and dissolution property thereof from the preparation, and found that the objects can be unexpectedly accomplished by the co-presence of a pH control agent and compound (I), and further, by adjusting, with a pH control agent, the pH range of a solid preparation thereof to a pH range in which the solubility of compound (I) becomes low. In addition, they have found that a diuretic and compound (I) containing a pH control agent can be further stabilized by separately granulating them, whereby a preparation more superior in the dissolution property of compound (I) as compared to general granulation preparations can be obtained, which resulted in the completion of the present invention.

Accordingly, the present invention relates to:

[1] a solid preparation comprising a compound represented by the formula (I):

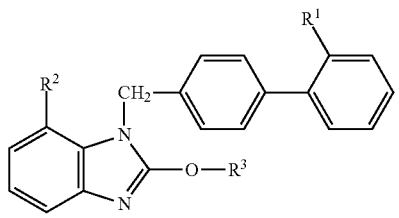

wherein $R^1$ is a monocyclic nitrogen-containing heterocyclic group having a deprotonizable hydrogen atom, $R^2$ is an esterified carboxyl group and $R^3$ is an optionally substituted lower alkyl, or a salt thereof, a pH control agent and a diuretic,

[2] the solid preparation of [1], wherein the compound represented by the formula (I) or a salt thereof is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt,

[3] the solid preparation of [1] or [2], wherein the diuretic is chlorthalidone or hydrochlorothiazide,

[4] the solid preparation of [1], wherein the salt of the compound represented by the formula (I) is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt, and the diuretic is chlorthalidone,

[5] the solid preparation of [1], wherein the pH control agent has pH 2 to 5,

[6] the solid preparation of [1], wherein the pH control agent is an acidic substance selected from the group consisting of tartaric acid, citric acid, lactic acid, fumaric acid, succinic acid, phosphoric acid, malic acid, ascorbic acid, acetic acid and acidic amino acid, or a salt thereof, or a solvate thereof,

[7] the solid preparation of [1], wherein the pH control agent is monosodium fumarate, or a combination of fumaric acid and sodium ion donor,

[8] a solid preparation comprising a first part comprising a compound represented by the formula (I):

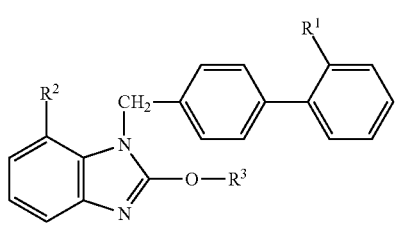

wherein $R^1$ is a monocyclic nitrogen-containing heterocyclic group having a deprotonizable hydrogen atom, $R^2$ is an esterified carboxyl group and $R^3$ is an optionally substituted lower alkyl, or a salt thereof and a pH control agent, and a second part comprising a diuretic, which is obtained by granulating separately from the first part,

[9] the solid preparation of [1], wherein the compound represented by the formula (I), or a salt thereof and the pH control agent are contained in a first part and the diuretic is contained in a second part, which is a multi-layer tablet comprising a first layer comprised of the first part and a second layer comprised of the second part,

[10] the solid preparation of [1], wherein the pH control agent is in a proportion of 0.01-20 wt % of the preparation,

[11] a method of stabilizing a compound represented by the formula (I) or a salt thereof and a diuretic in a solid preparation, which comprises adding a pH control agent to the solid preparation,

[12] a method of improving dissolution property of a compound represented by the formula (I) or a salt thereof from a solid preparation comprising the compound or the salt thereof and a diuretic, which comprises adding a pH control agent to the solid preparation;
and the like.

Effect of the Invention

The solid preparation of the present invention comprising compound (I), a pH control agent and a diuretic can provide a preparation superior in the stability and dissolution property of compound (I) and the diuretic.

DESCRIPTION OF EMBODIMENTS

Figure 1:
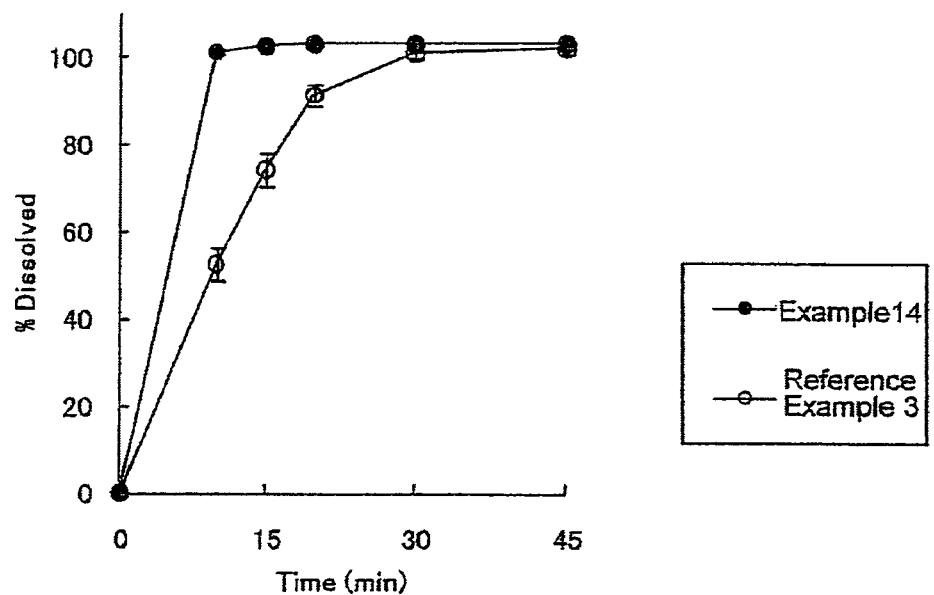
FIG. 1 shows dissolution profiles of the tablets obtained in Example 14 and Reference Example 3.

The solid preparation of the present invention is explained in detail in the following.

The solid preparation of the present invention contains compound (I), a pH control agent and a diuretic (also referred to as the solid preparation of the present invention). The solid preparation of the present invention is superior in the stability of compound (I), and also superior in the dissolution property of the compound (I). It is also superior in the stability of the diuretic.

In the aforementioned formula (I), $R^1$ is a monocyclic nitrogen-containing heterocyclic group having a hydrogen atom that can be deprotonized, such as a tetrazolyl group or a group represented by the formula

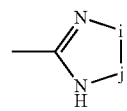

wherein i is —O— or —S—, j is >C=O, >C=S or >S(O)m wherein m is 0, 1 or 2 (e.g., 4,5-dihydro-5-oxo-1,2,4-oxadiazol-3-yl group, etc.) and the like are preferable.

A 4,5-dihydro-5-oxo-1,2,4-oxadiazol-3-yl group includes three tautomers (a', b' and c') represented by the formulas:

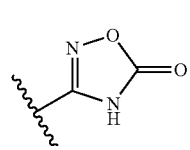

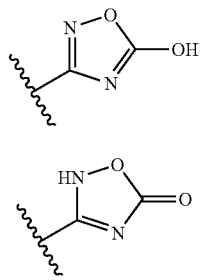

and 4,5-dihydro-5-oxo-1,2,4-oxadiazol-3-yl group includes all of the above-mentioned a', b' and c'.

In the aforementioned formula (I), $R^2$ is an esterified carboxyl group and, for example, preferably a carboxyl group esterified by lower ($C_{1-4}$)alkyl optionally substituted by a substituent selected from a hydroxyl group, an amino group, a halogen atom, lower ($C_{2-6}$)alkanoyloxy (e.g., acetyloxy, pivaloyloxy, etc.), lower ($C_{4-7}$)cycloalkanoyloxy, (lower ($C_{1-6}$)alkoxy)carbonyloxy (e.g., methoxycarbonyloxy, ethoxycarbonyloxy, etc.), (lower ($C_{3-7}$)cycloalkoxy)carbonyloxy (e.g., cyclohexyloxycarbonyloxy, etc.), lower ($C_{1-4}$)alkoxy and 5-methyl-2-oxo-1,3-dioxolen-4-yl (e.g., (5-methyl-2-oxo-1,3-dioxolen-4-yl)methoxycarbonyl group, 1-(cyclohexyloxycarbonyloxy)ethoxycarbonyl group and the like).

In the aforementioned formula (I), $R^3$ is an optionally substituted lower alkyl, and preferably a lower ($C_{1-5}$)alkyl optionally substituted by a substituent selected from a hydroxyl group, an amino group, a halogen atom and a lower ($C_{1-4}$)alkoxy group (preferably lower ($C_{2-3}$)alkyl; particularly preferably ethyl).

The salt of a compound represented by the formula (I) is, for example, a pharmaceutically acceptable salt. Examples of the salt of a compound represented by the formula (I) include a salt with an inorganic base, a salt with an organic base, a salt with an inorganic acid, a salt with an organic acid, a salt with a basic or acidic amino acid and the like. Preferable examples of the salt with an inorganic base include alkali metal salt such as sodium salt, potassium salt and the like; alkaline earth metal salt such as calcium salt, magnesium salt and the like; aluminum salt, ammonium salt and the like. Preferable examples of the salt with an organic base include salts with trimethylamine, triethylamine, pyridine, picoline, ethanolamine, diethanolamine, triethanolamine, dicyclohexylamine, N,N'-dibenzylethylenediamine and the like. Preferable examples of the salt with an inorganic acid include salts with hydrochloric acid, hydrobromic acid, nitric acid, sulfuric acid, phosphoric acid and the like. Preferable examples of the salt with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with a basic amino acid include salts with arginine, lysine, ornithine and the like, and preferable examples of salts with acidic amino acid include salts with aspartic acid, glutamic acid and the like.

As a compound represented by the formula (I) or a salt thereof, a salt of (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate is preferable, and (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt is particularly preferable.

The salt of a compound represented by the formula (I) may be hydrate or non-hydrate.

Compound (I) may be a solvate including hydrate or a non-solvate.

Compound (I) is preferably in the form of a crystal, and preferably has a melting point of 100-250° C., particularly 120-200° C., especially 130-180° C.

Compound (I) is contained in the solid preparation of the present invention in a proportion of 0.1-60 wt %, preferably 1-40 wt %, more preferably 5-30 wt %.

The pH control agent to be used in the present invention may be any as long as it simultaneously achieves stability of the preparation of compound (I) and dissolution property of compound (I) from the preparation and is applicable to a pharmaceutical product. In addition, plural pH control agents may be used in combination. The pH control agent to be used in the present invention preferably has a pH of about 2 to about 5, preferably about 3 to about 5, more preferably about 3 to about 4. For example, an acidic substance such as tartaric acid, citric acid, lactic acid, fumaric acid, phosphoric acid, malic acid, succinic acid, ascorbic acid, acetic acid, acidic amino acid (e.g., glutamic acid, aspartic acid) and the like, an inorganic salt (e.g., alkali metal salt, alkaline earth metal salt, ammonium salt and the like) of these acidic substances, a salt of such acidic substance with an organic base (e.g., basic amino acid such as lysine, arginine and the like, meglumine and the like), a solvate (e.g., hydrate) thereof and the like are used. The pH control agent simultaneously achieves stability of a diuretic and dissolution property of the diuretic from the preparation.

Here, the pH of the pH control agent is measured under the following conditions. To be specific, it is the pH of a solution or suspension obtained by dissolving or suspending a pH control agent in water at 25° C. at a concentration of 1 w/v %.

As the pH control agent to be used in the present invention, an acidic substance and a basic substance are combined, and the obtained pH control agent may be adjusted such that the pH of the solution or suspension is about 2 to about 5, preferably about 3 to about 5, more preferably about 3 to about 4, when the combined pH control agent is dissolved or suspended in water at 25° C. at a concentration of 1 w/v %. Examples of the acidic substance to be used in combination include, in addition to the acidic substances having a pH of about 2 to about 5 mentioned above and salts thereof, strong acids such as hydrochloric acid, sulfuric acid, phosphoric acid and like. Examples of the basic substance to be used in combination include inorganic bases (e.g., sodium hydroxide, potassium hydroxide, sodium carbonate, sodium hydrogen carbonate, magnesium carbonate, calcium carbonate, magnesium oxide, ammonia, synthetic hydrotalcite), organic bases (e.g., basic amino acid such as lysine, arginine, etc., meglumine, and the like) and the like.

The pH control agent to be used in the present invention preferably affords a solution having a buffering capacity at pH 2 to 5, such as sodium dihydrogen phosphate, monosodium fumarate, a combination of fumaric acid and sodium ion donor and the like.

The pH control agent to be used in the present invention is preferably monosodium fumarate or a combination of fumaric acid and sodium ion donor. In addition, fumaric acid and sodium hydroxide may be used in combination.

In the solid preparation of the present invention, the pH control agent is contained in a proportion of 0.01-20 wt %, preferably 0.05-10 wt %, more preferably 0.1-5 wt %, of the solid preparation.

Examples of the diuretic in the present invention include xanthine derivatives (e.g., theobromine sodium salicylate, theobromine calcium salicylate etc.), thiazide preparations (e.g., ethiazide, cyclopenthiazide, trichloromethyazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonic anhydrase inhibitors (e.g., acetazolamide etc.), chlorobenzenesulfonamide agents (e.g., chlorthalidone, mefruside, indapamide etc.), azosemide, isosorbide, ethacrynic acid, piretanide, bumetanide, furosemide and the like. The diuretic in the present invention also includes salts of the compounds recited as the above-mentioned diuretic.

As the diuretic in the present invention, a chlorobenzenesulfonamide agent, a thiazide preparation and the like are preferable, and chlorthalidone, hydrochlorothiazide and the like are more preferable. Especially, chlorthalidone is preferable.

In the present invention, the diuretic is contained in the solid preparation in a proportion of generally, 0.1-60 wt % (appropriately adjusted so that the total of compound (I) and pH control agent will not exceed 100%), preferably 0.5-40 wt %, more preferably 1-30 wt %. Specifically, chlorthalidone (converted into a free form) is contained in a proportion of generally 0.1-60 wt %, preferably 0.5-40 wt %, more preferably 1-30 wt %. Hydrochlorothiazide (converted into a free form) is contained in a proportion of generally 0.1-60 wt %, preferably 0.5-40 wt %, more preferably 1-30 wt %.

A preferable form of the solid preparation of the present invention is a preparation wherein compound (I) is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and the diuretic is chlorthalidone.

Examples of the solid preparation of the present invention include a solid preparation suitable for oral administration such as tablets, granules, fine granules, capsules, pills and the like.

Therefore, the embodiments of the solid preparation of the present invention include the following preparations.

(1) A solid preparation obtained by mixing and granulating compound (I), a pH control agent and a diuretic (single granulation preparation).

(2) A solid preparation containing a first part containing compound (I) and a pH control agent, and a second part containing a diuretic, which is obtained by separately granulating the first part and the second part (separating granulation preparation—a single layer tablet).

(3) A solid preparation obtained by compression-molding a first part containing compound (I) and a pH control agent, and a second part containing a diuretic independently, which are separately granulated (separating granulation preparation—a multi-layer tablet), or by coating one part with the other part, which are separately granulated (separating granulation preparation—coated tablet).

The solid preparation of the above-mentioned (1) simultaneously achieves dissolution property and stability of compound (I) and a diuretic respectively in and from the preparation thereof by the addition of a pH control agent. In the above-mentioned (2) and (3), the dissolution property and stability of compound (I) and the diuretic are respectively improved further.

The solid preparation of the above-mentioned (1) can be produced by a method known per se (e.g., method described in the Japanese Pharmacopoeia 14$^{th}$ Edition, General Rules for Preparations).

For example, compound (I), a pH control agent, a diuretic, additives and the like are mixed, a binder is added to the mixture to give granules, a lubricant and the like are added to the granules and the mixture is tableted into a tablet. Granules and fine granules can also be produced by a method similar to that of the tablet.

In the case of a capsule, the above-mentioned granules and fine granules are filled in a capsule containing gelatin, hydroxypropylmethylcellulose and the like. Alternatively, an active ingredient and a filler are filled in a capsule containing gelatin, hydroxypropylmethylcellulose and the like.

The solid preparation may contain additives conventionally used in the pharmaceutical field. Examples of the additive include filler, disintegrant, binder, lubricant, colorant, pH control agent, surfactant, stabilizer, acidulant, flavor, glidant and the like. These additives are used in an amount conventionally employed in the pharmaceutical field.

Examples of the filler include starches such as cornstarch, potato starch, wheat starch, rice starch, partly pregelatinized starch, pregelatinized starch, porous starch and the like; sugar and sugar alcohols such as lactose, fructose, glucose, mannitol (e.g., D-mannitol), sorbitol (e.g., D-sorbitol), erythritol (e.g., D-erythritol), sucrose and the like; anhydrous calcium phosphate, crystalline cellulose, microcrystalline cellulose, glycyrrhiza uralensis, sodium hydrogen carbonate, calcium phosphate, calcium sulfate, calcium carbonate, precipitated calcium carbonate, calcium silicate and the like.

Examples of the disintegrant include amino acid, starch, cornstarch, carboxymethylcellulose, calcium carboxymethylcellulose, sodium carboxymethyl starch, carmellose sodium, carmellose calcium, croscarmellose sodium, crospovidone, low-substituted hydroxypropylcellulose, hydroxypropylstarch, sodium carboxymethyl starch and the like.

Examples of the binder include crystalline cellulose (e.g., microcrystalline cellulose), hydroxypropylcellulose, hydroxypropylmethylcellulose, polyvinylpyrrolidone, gelatin, starch, gum arabic powder, tragacanth, carboxymethylcellulose, sodium alginate, pullulan, glycerol and the like.

Preferable examples of the lubricant include magnesium stearate, stearic acid, calcium stearate, talc (purified talc), sucrose esters of fatty acids, stearyl fumarate monosodium salt and the like.

Examples of the colorant include food colors such as Food Color Yellow No. 5, Food Color Red No. 2, Food Color Blue No. 2 and the like, food lake colors, diiron trioxide and the like.

Examples of the surfactant include sodium lauryl sulfate, polysorbate 80, polyoxyethylene(160)polyoxypropylene(30) glycol and the like.

Examples of the stabilizer include tocopherol, tetrasodium edetate, nicotinic acid amide, cyclodextrins and the like.

Examples of the acidulant include ascorbic acid, citric acid, tartaric acid, malic acid and the like.

Examples of the flavor include menthol, peppermint oil, lemon oil, vanillin and the like.

Examples of the glidant include light anhydrous silicic acid, hydrated silicon dioxide and the like.

The above-mentioned additives may be a mixture of two or more kinds at an appropriate ratio.

The solid preparation of the above-mentioned (2) contains a first part and a second part, which are separately granulated, and can be produced by a method known per se.

In the solid preparation of the above-mentioned (2), the first part in the present invention is a part (composition) containing compound (I) and a pH control agent.

The amount of the pH control agent to be used in the present invention is preferably 0.01-20 parts by weight, preferably 0.05-10 parts by weight, more preferably 0.1-5 parts by weight, per 100 parts by weight of the above-mentioned first part.

The weight ratio of compound (I) to a pH control agent (compound (I):pH control agent) is preferably 1-30:1, more preferably 5-25:1, more preferably 10-20:1.

The above-mentioned first part is not limited as long as it has a shape and a size that afford a solid preparation together with the below-mentioned second part.

The above-mentioned first part may further contain additives conventionally used in the pharmaceutical field. As the additives, those similar to the aforementioned additives can be used.

The above-mentioned first part can be produced by mixing compound (I), a pH control agent and, where necessary, the above-mentioned additives and granulating the mixture according to a method known per se.

The above-mentioned first part preferably contains compound (I) (preferably (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt); a pH control agent (preferably fumaric acid and sodium hydroxide); a filler (preferably mannitol and crystalline cellulose); and a binder (preferably hydroxypropylcellulose).

The second part in the present invention is a part (composition) containing a diuretic.

The above-mentioned second part is not limited as long as it has a shape and a size that afford a solid preparation together with the above-mentioned first part.

The above-mentioned second part may further contain additives conventionally used in the pharmaceutical field. As the additives, those similar to the aforementioned additives can be used.

Specifically, it contains a diuretic (preferably chlorthalidone); a filler (preferably mannitol and crystalline cellulose); and a binder (preferably hydroxypropylcellulose).

The above-mentioned second part can be produced by mixing a diuretic and, where necessary, the above-mentioned additives and granulating the mixture according to a method known per se.

The amount of the diuretic is preferably 0.1-60 parts by weight, more preferably 0.5-40 parts by weight, more preferably 1-30 parts by weight, per 100 parts by weight of the above-mentioned second part.

The weight ratio of the second part to the first part in the solid preparation of the present invention (second part:first part) is preferably 0.1-10:1, more preferably 0.3-5:1, more preferably, 0.5-3:1.

A single layer tablet produced by mixing a first part and a second part, which are separately granulated, and further, additives conventionally used in the pharmaceutical field, and then compressing the mixture is also encompassed in the solid preparation of the present invention. A capsule produced by filling the above-mentioned single layer tablet in a capsule (e.g., hydroxypropylmethylcellulose capsule) is also encompassed in the solid preparation of the present invention.

A capsule produced by directly filling the first part and the second part, which are separately granulated, or together with the above-mentioned additives, in a capsule (e.g., hydroxypropylmethylcellulose capsule) is also encompassed in the solid preparation of the present invention.

In the solid preparation of the above-mentioned (3), the first part and the second part are separately granulated, and the preparation can be produced by compressing independently these parts, or coating one part with the other part.

Specific examples of the solid preparation of the above-mentioned (3) include [1] coated tablet (A) containing an inner core of the first part and an outer layer of the second part; [2] coated tablet (B) containing an inner core of the second part and an outer layer of the first part; [3] a multi-layer tablet containing a first layer of the first part and a second layer of the second part.

The inner core of the first part can be produced by, for example, granulating compound (I), a pH control agent and, where necessary, additives. After granulation, where necessary, an operation of drying, sieving, compression and the like may be applied.

The outer layer of the second part can be produced, for example, by granulating a diuretic (e.g., chlorthalidone or a salt thereof) with additives, as necessary.

The coating can be performed, for example, by compression, coating and the like. The additive is preferably a binder and the like.

For production of coated tablet (A), an inactive intermediate layer may be inserted between an inner core and an outer layer to prevent a direct contact. The intermediate layer contains, for example, the following coating base and additives for coating. The intermediate layer preferably contains a water-soluble film coating base and a glidant.

The above-mentioned coated tablet (B) can be produced in the same manner as in coated tablet (A) except that the second part is used as an inner core and first part is used as an outer layer.

The multi-layer tablet of the present invention comprises a first part containing a compound represented by the formula (I) or a salt thereof and a pH control agent and a second part containing a diuretic, wherein a first layer is comprised of the first part and a second layer is comprised of the second part.

The multi-layer tablet of the present invention is not particularly limited as long as it is a preparation wherein at least the first layer comprised of the first part and the second layer comprised of the second part are integrally formed.

In addition, the multi-layer tablet in the present invention may have an inactive intermediate layer between the first layer and the second layer.

When the multi-layer tablet in the present invention has such intermediate layer, the adverse influences (decreased preservation stability such as time-course decomposition of active ingredients, lowered effectiveness and the like, decreased dissolution stability such as time-course changes in dissolution pattern of active ingredients and the like, and so on) produced by interaction between the active ingredients can be more effectively suppressed.

The multi-layer tablet can be produced, for example, by the following production steps.

Compound (I) and a pH control agent are mixed with additives as necessary, and the obtained mixture is granulated to give the first part. After granulation, operations such as drying, sieving and the like may be performed where necessary. Thereafter, additives are mixed where necessary to give the first layer.

Then, a diuretic is granulated with additives as necessary, and the obtained second part is mixed with additives as necessary to give the second layer, which is put on the above-mentioned first layer in layers and compressed (preferably tableted).

To prevent a direct contact of respective layers, an inactive intermediate layer may be inserted between the respective layers. The intermediate layer contains, for example, the above-mentioned filler, disintegrant, binder, lubricant, colorant and the like.

A capsule produced by filling the above-mentioned coated tablet (A) or (B) or multi-layer tablet in a capsule (e.g., a hydroxypropylmethylcellulose capsule) is also encompassed in the solid preparation of the present invention.

In addition, a film coating preparation produced by coating the above-mentioned solid preparation (1)-(3) with a film of the following coating base and additives for coating is also encompassed in the solid preparation of the present invention.

Preferable examples of the coating base include a sugar coating base, a water-soluble film coating base, an enteric film coating base, a sustained-release film coating base and the like.

As the sugar coating base, sucrose is used. Moreover, one or more kinds selected from talc, precipitated calcium carbonate, gelatin, gum arabic, pullulan, carnauba wax and the like may also be used concurrently.

Examples of the water-soluble film coating base include cellulose polymers such as hydroxypropylcellulose [e.g., grade: L, SL, SL-T, SSL (trade name); Nippon Soda Co., Ltd.], hydroxypropylmethylcellulose [e.g., TC-5 (grade: MW, E, EW, R, RW) (trade name); Shin-Etsu Chemical Co., Ltd.], hydroxyethylcellulose, methylhydroxyethylcellulose and the like; synthetic polymers such as polyvinyl acetaldiethylaminoacetate, aminoalkylmethacrylate copolymer E [Eudragit E (trade name)], polyvinylpyrrolidone and the like; polysaccharides such as pullulan and the like, and so on.

Examples of the enteric film coating base include cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substance such as shellac and the like, and so on.

Examples of the sustained-release film coating base include cellulose polymers such as ethylcellulose and the like; acrylic acid polymers such as aminoalkylmethacrylate copolymer RS [Eudragit RS (trade name)], ethyl acrylate-methyl methacrylate copolymer suspension [Eudragit NE (trade name)] and the like, and so on.

Preferable examples of the coating additives include light protecting agents such as titanium oxide and the like, glidants such as talc and the like, colorants such as red ferric oxide, yellow ferric oxide and the like; plasticizers such as polyethylene glycol [e.g., macrogol 6000 (trade name)], triethyl citrate, castor oil, polysorbate and the like; organic acids such as citric acid, tartaric acid, malic acid, ascorbic acid and the like; and so on.

Moreover, the solid preparation of the present invention may have a distinguishable embossing or printed letters, or a scored line for division.

The solid preparation of the present invention is preferably film-coated from the aspects of easy administration, mechanical strength and the like.

In the aforementioned production steps, operations such as mixing, compression, coating and the like are performed according to the methods conventionally used in the pharmaceutical technological field.

The mixing is performed, for example, using a blending machine such as a V-type mixer, a tumbler mixer and the like; and a granulator such as a high speed mixer granulator, a fluid bed granulator, an extrusion-granulator, a roller compactor and the like.

The compression is performed, for example, using a single stroke tableting machine, a rotary tableting machine and the like.

When compression is performed using a single stroke tableting machine, a rotary tableting machine and the like, a tableting pressure of generally 1-20 kN/cm$^2$ (preferably 5-15 kN/cm$^2$) is preferably employed. In addition, a taper cutting die is preferably used for preventing capping.

The coating is performed, for example, using a film coating apparatus and the like.

The solid preparation of the present invention can be used safely as a medicine for mammals (e.g., human, dog, rabbit, rat, mouse and the like).

While the dose of compound (I) to patients is determined in consideration of age, body weight, general health condition, sex, diet, administration time, clearance rate, combination of drugs and the like, as well as the severity of the disease for which the patient is undergoing treatments, the daily dose is about 0.05-500 mg, preferably 0.1-100 mg.

While the dose of a diuretic to patients is determined in consideration of age, body weight, general health condition, sex, diet, administration time, clearance rate, combination of drugs and the like, as well as the severity of the disease for which the patient is undergoing treatments, the daily dose is, for example, about 12.5-100 mg, preferably 15-50 mg, of chlorthalidone (converted into free form). In the case of hydrochlorothiazide (converted into free form), the daily dose is about 12.5-100 mg, preferably 15-50 mg.

Since compound (I) has a strong angiotensin II antagonistic activity, the pharmaceutical composition of the present invention is useful as a prophylactic or therapeutic drug for diseases developed by (or diseases whose onset is promoted by) contraction or growth of blood vessel or an organ disorder expressed via angiotensin II receptor, due to the presence of angiotensin II, or a factor induced by the presence of angiotensin II, in mammals (e.g., human, monkey, cat, swine, horse, bovine, mouse, rat, guinea pig, dog, rabbit and the like).

By combination of compound (I) and a diuretic, the solid preparation of the present invention is useful as a prophylactic or therapeutic drug for the above-mentioned diseases, can reduce the doses of compound (I) and a diuretic as compared to independent use thereof and can suppress expression of side effects.

The present invention provides a method of stabilizing a compound represented by the formula (I) or a salt thereof and a diuretic in a solid preparation containing a compound represented by the formula (I) or a salt thereof, and a diuretic, which includes adding a pH control agent. According to the stabilizing method of the present invention, compound (I) and a diuretic in a solid preparation is significantly stabilized. In addition, the present invention provides a method of improving dissolution of a compound represented by the formula (I) or a salt thereof from a solid preparation containing the compound or a salt thereof, and a diuretic, which includes adding a pH control agent. According to the improving method of dissolution property in the present invention, the dissolution property of compound (I) and a diuretic from a solid preparation is significantly improved.

EXAMPLES

The present invention is explained in more detail in the following by referring to Examples and Experimental Examples, which are not to be construed as limitative.

In the formulations described in the Example, the components (additives) other than the active ingredient may be those recited in the Japanese Pharmacopoeia, the Japanese Pharmacopoeia Japanese Pharmaceutical Codex or Japanese Pharmaceutical Excipients and the like.

Example 1

(1) In a fluid bed granulator (FD-5S, POWREX CORPORATION), (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt (hereinafter to be referred to as compound A) (1067 g) and mannitol (1968 g) were uniformly mixed, granulated by spraying an aqueous solution of hydroxypropylcellulose (112.5 g), fumaric acid (46.5 g) and sodium hydroxide (16 g), and dried therein to give granules. The obtained granules were passed through a 16 mesh sieve (aperture 1.0 mm) to give sieved granules A.

(2) In a fluid bed granulator (Lab-1, POWREX CORPORATION), chlorthalidone (300 g), and mannitol (402 g) were uniformly mixed, granulated by spraying an aqueous solution of hydroxypropylcellulose (27 g), and dried therein to give granules. The obtained granules were passed through a 16 mesh sieve (aperture 1.0 mm) to give sieved granules B.

(3) Croscarmellose sodium (24.68 g), crystalline cellulose (30.86 g), magnesium stearate (3.08 g), the sieved granules A (128.4 g) and the sieved granules B (121.5 g) were mixed in a bag to give mixed granules.

(4) The mixed granules were tableted by a rotary tableting machine (AQUARIUS, Kikusui Seisakusho, Ltd.) using a 7 mmϕ punch (tableting pressure: 4 KN/punch, weight per tablet: 154.26 mg) to give core tablets having the following composition. Then, the core tablets were dried under the reduced pressure at 40° C. for 16 hr.

Composition of Preparation (154.26 mg)

| | |
|---|---|
| compound A | 21.34 mg |
| mannitol | 39.36 mg |
| hydroxypropylcellulose | 2.25 mg |
| fumaric acid | 0.93 mg |
| sodium hydroxide | 0.32 mg |
| chlorthalidone | 25 mg |
| mannitol | 33.5 mg |
| hydroxypropylcellulose | 2.25 mg |
| croscarmellose sodium | 12.34 mg |
| crystalline cellulose | 15.43 mg |
| magnesium stearate | 1.54 mg |
| total | 154.26 mg |

Example 2

(1) In a fluid bed granulator (Lab-1, POWREX CORPORATION), compound A (256.1 g) and mannitol (429.8 g) were uniformly mixed, granulated by spraying an aqueous solution of hydroxypropylcellulose (27 g), fumaric acid (12 g) and sodium hydroxide (4.14 g), and dried therein to give granules. The obtained granules were passed through a 16 mesh sieve (aperture 1.0 mm) to give sieved granules A. Croscarmellose sodium (24 g), crystalline cellulose (30 g) and magnesium stearate (3 g) and the sieved granules A (85.36 g) were mixed in a bag to give mixed granules A.

(2) Crystalline cellulose (granules) was fed into a rotating fluid bed granulator (SPIR-A-FLOW, Freund Corporation), and a dispersion of chlorthalidone (105 g), crystalline cellulose (6.3 g), low-substituted hydroxypropylcellulose (16.8 g) hydroxypropylmethylcellulose (16.8 g) was sprayed and layered on the crystalline cellulose granules, and dried therein to give granules. The obtained granules were passed through a sieve to give sieved granules B (150-500 μm).

(3) The mixed granules A (3 g) and the sieved granules B (0.525 g) were mixed in a glass bottle to give mixed granules. The obtained mixed granules were tableted by Autograph (SHIMADZU Corporation, AG-5000B) using a 9.5 mmϕ punch (tableting pressure: 7 KN/punch, weight per tablet: 352.5 mg) to give core tablets having the following composition. Then, the core tablets were dried under the reduced pressure at 40° C. for 16 hr.

Composition of Preparation (352.5 mg)

| | |
|---|---|
| compound A | 85.36 mg |
| mannitol | 143.26 mg |
| hydroxypropylcellulose | 9 mg |
| fumaric acid | 4 mg |
| sodium hydroxide | 1.38 mg |
| chlorthalidone | 25 mg |
| crystalline cellulose (granules) | 18 mg |
| crystalline cellulose | 1.5 mg |
| low-substituted hydroxypropylcellulose | 4 mg |
| hydroxypropylmethylcellulose | 4 mg |
| croscarmellose sodium | 24 mg |
| crystalline cellulose | 30 mg |
| magnesium stearate | 3 mg |
| total | 352.5 mg |

Example 3

(1) Hydroxypropylcellulose (2800 g) was dissolved in purified water (44070 g) to give liquid I. In a fluid bed granulator (WSG-60, POWREX CORPORATION), chlorthalidone (5375 g), mannitol (53450 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules B.

(3) Crystalline cellulose (9720 g), crospovidone (5670 g), magnesium stearate (972 g), the milled granules A (54430 g) and the milled granules B (26410 g) were mixed in a tumbler mixer (TM-400S, Showa Chemical Machinery) to give mixed granules.

(4) The mixed granules were tableted by a rotary tableting machine (AQUARIUS36K, Kikusui Seisakusho, Ltd.) using a 8.5 mmϕ punch (tableting pressure: 8 kN, weight per tablet: 270 mg) to give core tablets.

(5) Hydroxypropylmethylcellulose (4095 g) and talc (630 g) were dissolved and dispersed in purified water (37800 g) to give dispersion liquid I. Titanium oxide (493.5 g) and iron oxide (31.5 g) were dispersed in purified water (9450 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 10 mg per tablet to give film-coated tablets having the following composition. Then, the film-coated tablets were dried under the reduced pressure at 40° C. for 15 hr.

Composition of Preparation (280 mg)

| | |
|---|---:|
| chlorthalidone | 12.5 mg |
| mannitol | 124.3 mg |
| crystalline cellulose | 9 mg |
| hydroxypropylcellulose | 5.4 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 27 mg |
| crospovidone | 15.75 mg |
| magnesium stearate | 2.7 mg |
| hydroxypropylmethylcellulose | 7.8 mg |
| talc | 1.2 mg |
| titanium oxide | 0.94 mg |
| iron oxide | 0.06 mg |
| total | 280 mg |

Example 4

(1) Hydroxypropylcellulose (2800 g) was dissolved in purified water (44070 g) to give liquid I. In a fluid bed granulator (WSG-60, POWREX CORPORATION), chlorthalidone (10750 g), mannitol (48070 g) and crystalline cellulose (3870 g) were uniformly mixed, granulated by spraying liquid I (38870 g), and dried to give granules. A part of the obtained granules was milled in a powermill grinder (P-7S, Showa Chemical Machinery) using a 1.5 mmϕ punching screen to give milled granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules B.
(3) Crystalline cellulose (9720 g), crospovidone (5670 g), magnesium stearate (972 g), milled granules A (54430 g) and the milled granules B (26410 g) were mixed in a tumbler mixer (TM-400S, Showa Chemical Machinery) to give mixed granules.
(4) The mixed granules were tableted by a rotary tableting machine (AQUARIUS36K, Kikusui Seisakusho, Ltd.) using a 8.5 mmϕ punch (tableting pressure: 8 kN, weight per tablet: 270 mg) to give core tablets.
(5) Hydroxypropylmethylcellulose (4095 g) and talc (630 g) were dissolved and dispersed in purified water (37800 g) to give dispersion liquid I. Titanium oxide (493.5 g) and iron oxide (31.5 g) were dispersed in purified water (9450 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 10 mg per tablet to give film-coated tablets having the following composition. Then, the film-coated tablets were dried under the reduced pressure at 40° C. for 15 hr.

Composition of Preparation (280 mg)

| | |
|---|---:|
| chlorthalidone | 25 mg |
| mannitol | 111.8 mg |
| crystalline cellulose | 9 mg |
| hydroxypropylcellulose | 5.4 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 27 mg |
| crospovidone | 15.75 mg |
| magnesium stearate | 2.7 mg |
| hydroxypropylmethylcellulose | 7.8 mg |
| talc | 1.2 mg |
| titanium oxide | 0.94 mg |
| iron oxide | 0.06 mg |
| total | 280 mg |

Example 5

(1) Hydroxypropylcellulose (2800 g) was dissolved in purified water (44070 g) to give liquid I. In a fluid bed granulator (WSG-60, POWREX CORPORATION), chlorthalidone (5375 g), mannitol (53450 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules B.
(3) Crystalline cellulose (9720 g), crospovidone (6075 g), magnesium stearate (972 g), the milled granules A (40820 g) and the milled granules B (39610 g) were mixed in a tumbler mixer (TM-400S, Showa Chemical Machinery) to give mixed granules.
(4) The mixed granules were tableted by a rotary tableting machine (AQUARIUS36K, Kikusui Seisakusho, Ltd.) using a 9.5 mmϕ punch (tableting pressure: 9 kN, weight per tablet: 360 mg) to give core tablets.
(5) Hydroxypropylmethylcellulose (3471 g) and talc (534 g) were dissolved and dispersed in purified water (32040 g) to give dispersion liquid I. Titanium oxide (418.3 g) and iron oxide (26.7 g) were dispersed in purified water (8010 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 10 mg per tablet to give film-coated tablets having the following composition. Then, the film-coated tablets were dried under the reduced pressure at 40° C. for 15 hr.

Composition of Preparation (370 mg)

| | |
|---|---:|
| chlorthalidone | 12.5 mg |
| mannitol | 124.3 mg |
| crystalline cellulose | 9 mg |
| hydroxypropylcellulose | 5.4 mg |
| compound A | 42.68 mg |
| mannitol | 86.93 mg |
| crystalline cellulose | 9 mg |
| sodium hydroxide | 0.69 mg |
| fumaric acid | 2 mg |
| hydroxypropylcellulose | 5.4 mg |
| crystalline cellulose | 36 mg |
| crospovidone | 22.5 mg |
| magnesium stearate | 3.6 mg |
| hydroxypropylmethyl cellulose | 7.8 mg |
| talc | 1.2 mg |
| titanium oxide | 0.94 mg |
| iron oxide | 0.06 mg |
| total | 370 mg |

Example 6

(1) Hydroxypropylcellulose (2800 g) was dissolved in purified water (44070 g) to give liquid I. In a fluid bed granulator (WSG-60, POWREX CORPORATION), chlorthalidone (5375 g), mannitol (53450 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmφ punching screen to give milled granules B.
(3) Crystalline cellulose (9720 g), crospovidone (6075 g), magnesium stearate (972 g), the milled granules A (40820 g) and the milled granules B (39610 g) were mixed in a tumbler mixer (TM-400S, Showa Chemical Machinery) to give mixed granules.
(4) The mixed granules were tableted by a rotary tableting machine (AQUARIUS36K, Kikusui Seisakusho, Ltd.) using a 9.5 mmφ punch (tableting pressure: 9 kN, weight per tablet: 360 mg) to give core tablets.
(5) Hydroxypropylmethylcellulose (3471 g) and talc (534 g) were dissolved and dispersed in purified water (32040 g) to give dispersion liquid I. Titanium oxide (418.3 g) and iron oxide (26.7 g) were dispersed in purified water (8010 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 10 mg per tablet to give film-coated tablets having the following composition. Then, the film-coated tablets were dried under the reduced pressure at 40° C. for 15 hr.

Composition of Preparation (370 mg)

| | |
|---|---:|
| chlorthalidone | 25 mg |
| mannitol | 111.8 mg |
| crystalline cellulose | 9 mg |
| hydroxypropylcellulose | 5.4 mg |
| compound A | 42.68 mg |
| mannitol | 86.93 mg |
| crystalline cellulose | 9 mg |
| sodium hydroxide | 0.69 mg |
| fumaric acid | 2 mg |
| hydroxypropylcellulose | 5.4 mg |
| crystalline cellulose | 36 mg |
| crospovidone | 22.5 mg |
| magnesium stearate | 3.6 mg |
| hydroxypropylmethylcellulose | 7.8 mg |
| talc | 1.2 mg |
| titanium oxide | 0.94 mg |
| iron oxide | 0.06 mg |
| total | 370 mg |

Example 7

(1) Hydroxypropylcellulose (2800 g) was dissolved in purified water (44070 g) to give liquid I. In a fluid bed granulator (WSG-60, POWREX CORPORATION), chlorthalidone (5375 g), mannitol (53450 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmφ punching screen to give milled granules B.
(3) Crystalline cellulose (9720 g), crospovidone (6480 g), magnesium stearate (972 g), the milled granules A (27220 g) and the milled granules B (52810 g) were mixed in a tumbler mixer (TM-400S, Showa Chemical Machinery) to give mixed granules.
(4) The mixed granules were tableted by a rotary tableting machine (AQUARIUS36K, Kikusui Seisakusho, Ltd.) using a punch (major diameter 14 mm, minor diameter 8 mm) (tableting pressure: 10 kN, weight per tablet: 540 mg) to give core tablets.
(5) Hydroxypropylmethylcellulose (4056 g) and talc (624 g) were dissolved and dispersed in purified water (37440 g) to give dispersion liquid I. Titanium oxide (488.8 g) and iron oxide (31.2 g) were dispersed in purified water (9360 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 20 mg per tablet to give film-coated tablets having the following composition. Then, the film-coated tablets were dried under the reduced pressure at 40° C. for 15 hr.

Composition of Preparation (560 mg)

| | |
|---|---:|
| chlorthalidone | 12.5 mg |
| mannitol | 124.3 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 54 mg |
| crospovidone | 36 mg |
| magnesium stearate | 5.4 mg |
| hydroxypropylmethylcellulose | 15.6 mg |
| talc | 2.4 mg |
| titanium oxide | 1.88 mg |
| iron oxide | 0.12 mg |
| total | 560 mg |

Example 8

(1) Hydroxypropylcellulose (2800 g) was dissolved in purified water (44070 g) to give liquid I. In a fluid bed granulator (WSG-60, POWREX CORPORATION), chlorthalidone (10750 g), mannitol (48070 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules B.
(3) Crystalline cellulose (9720 g), crospovidone (6480 g), magnesium stearate (972 g), the milled granules A (27220 g) and the milled granules B (52810 g) were mixed in a tumbler mixer (TM-400S, Showa Chemical Machinery) to give mixed granules.
(4) The mixed granules were tableted by a rotary tableting machine (AQUARIUS36K, Kikusui Seisakusho, Ltd.) using a punch (major diameter 14 mm, minor diameter 8 mm) (tableting pressure: 10 kN, weight per tablet: 540 mg) to give core tablets.
(5) Hydroxypropylmethylcellulose (4056 g) and talc (624 g) were dissolved and dispersed in purified water (37440 g) to give dispersion liquid I. Titanium oxide (488.8 g) and iron oxide (31.2 g) were dispersed in purified water (9360 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (4) until the weight of the core tablet increased to 20 mg per tablet to give film-coated tablets having the following composition. Then, the film-coated tablets were dried under the reduced pressure at 40° C. for 15 hr.

Composition of Preparation (560 mg)

| | |
|---|---:|
| chlorthalidone | 25 mg |
| mannitol | 111.8 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 54 mg |
| crospovidone | 36 mg |
| magnesium stearate | 5.4 mg |
| hydroxypropylmethylcellulose | 15.6 mg |
| talc | 2.4 mg |
| titanium oxide | 1.88 mg |
| iron oxide | 0.12 mg |
| total | 560 mg |

Example 9

(1) Hydroxypropylcellulose (2800 g) was dissolved in purified water (44070 g) to give liquid I. In a fluid bed granulator (WSG-60, POWREX CORPORATION), chlorthalidone (10750 g), mannitol (48070 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.
(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (5400 g), magnesium stearate (720 g) and the milled granules (58680 g) were mixed in a tumbler mixer (TM-400S, Showa Chemical Machinery) to give mixed granules B.
(3) The mixed granules A (180 mg) and the mixed granules B (90 mg) were tableted in the form of a bilayer by a rotary tableting machine (AQUA08242L2JI, Kikusui Seisakusho, Ltd.) using a 8.5 mmϕ punch (tableting pressure: 7 kN, weight per tablet: 270 mg) to give core tablets.
(4) Hydroxypropylmethylcellulose (780 g) and talc (120 g) were dissolved and dispersed in purified water (7750 g) to give dispersion liquid I. Titanium oxide (94 g) and iron oxide (6 g) were dispersed in purified water (1000 g) to give dispersion liquid II. Dispersion liquid II and purified water (250 g) were added to dispersion liquid I, and the mixture was stirred to give a coating dispersion. Using a pan coating machine (DRC-650, POWREX CORPORATION), the coating dispersion was sprayed on the core tablets obtained in (3) until the weight of the core tablet increased to 10 mg per tablet to give film-coated tablets having the following composition. Then, the film-coated tablets were dried under the reduced pressure at 40° C. for 15 hr.
Composition of Preparation (280 mg)

| | |
|---|---:|
| chlorthalidone | 12.5 mg |
| mannitol | 124.3 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 9 mg |
| crospovidone | 6.75 mg |
| magnesium stearate | 0.9 mg |
| hydroxypropylmethylcellulose | 7.8 mg |
| talc | 1.2 mg |
| titanium oxide | 0.94 mg |
| iron oxide | 0.06 mg |
| total | 280 mg |

Example 10

(1) Hydroxypropylcellulose (5122 g) was dissolved in purified water (80620 g) to give liquid I. In a fluid bed granulator (WSG-60, POWREX CORPORATION), chlorthalidone (10740 g), mannitol (48080 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (5400 g), magnesium stearate (720 g) and the milled granules (58680 g) were mixed in a tumbler mixer (TM-400S, Showa Chemical Machinery) to give mixed granules B.

(3) The mixed granules A (180 mg) and the mixed granules B (90 mg) were tableted in the form of a bilayer by a rotary tableting machine (AQUA08242L2JI, Kikusui Seisakusho, Ltd.) using a 8.5 mmϕ punch (tableting pressure: 7 kN, weight per tablet: 270 mg) to give core tablets.

(4) Hydroxypropylmethylcellulose (780 g) and talc (120 g) were dissolved and dispersed in purified water (7750 g) to give dispersion liquid I. Titanium oxide (94 g) and iron oxide (6 g) were dispersed in purified water (1000 g) to give dispersion liquid II. Dispersion liquid II and purified water (250 g) were added to dispersion liquid I, and the mixture was stirred to give a coating dispersion. Using a pan coating machine (DRC-650, POWREX CORPORATION), the coating dispersion was sprayed on the core tablets obtained in (3) until the weight of the core tablet increased to 10 mg per tablet to give film-coated tablets having the following composition. Then, the film-coated tablets were dried under the reduced pressure at 40° C. for 15 hr.
Composition of Preparation (280 mg)

| | |
|---|---:|
| chlorthalidone | 25 mg |
| mannitol | 111.8 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 21.34 mg |
| mannitol | 43.465 mg |
| crystalline cellulose | 4.5 mg |
| sodium hydroxide | 0.345 mg |
| fumaric acid | 1 mg |
| hydroxypropylcellulose | 2.7 mg |
| crystalline cellulose | 9 mg |
| crospovidone | 6.75 mg |
| magnesium stearate | 0.9 mg |
| hydroxypropylmethylcellulose | 7.8 mg |
| talc | 1.2 mg |
| titanium oxide | 0.94 mg |
| iron oxide | 0.06 mg |
| total | 280 mg |

Example 11

(1) Hydroxypropylcellulose (2800 g) was dissolved in purified water (44070 g) to give liquid I. In a fluid bed granulator (WSG-60, POWREX CORPORATION), chlorthalidone (5375 g), mannitol (53450 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmϕ punching screen to give milled granules. Crystalline cellulose (7200 g), crospovidone (5400 g), magnesium stearate (720 g) and the milled granules (58680 g) were mixed in a tumbler mixer (TM-400S, Showa Chemical Machinery) to give mixed granules B.

(3) The mixed granules A (180 mg) and the mixed granules B (360 mg) were tableted in the form of a bilayer by a rotary tableting machine (AQUA08242L2JI, Kikusui Seisakusho, Ltd.) using a punch (major diameter 14 mm, minor diameter 8 mm) (tableting pressure: 10 kN, weight per tablet: 540 mg) to give core tablets.

(4) Hydroxypropylmethylcellulose (780 g) and talc (120 g) were dissolved and dispersed in purified water (7750 g) to give dispersion liquid I. Titanium oxide (94 g) and iron oxide (6 g) were dispersed in purified water (1000 g) to give dispersion liquid II. Dispersion liquid II and purified water (250 g) were added to dispersion liquid I, and the mixture was stirred to give a coating dispersion. Using a pan coating machine (DRC-650, POWREX CORPORATION), the coating dispersion was sprayed on the core tablets obtained in (3) until the weight of the core tablet increased to 20 mg per tablet to give film-coated tablets having the following composition. Then, the film-coated tablets were dried under the reduced pressure at 40° C. for 15 hr.

Composition of Preparation (560 mg)

| | |
|---|---:|
| chlorthalidone | 12.5 mg |
| mannitol | 124.3 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.88 mg |
| iron oxide | 0.12 mg |
| total | 560 mg |

Example 12

(1) Hydroxypropylcellulose (5122 g) was dissolved in purified water (80620 g) to give liquid I. In a fluid bed granulator (WSG-60, POWREX CORPORATION), chlorthalidone (10740 g), mannitol (48080 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules. Crystalline cellulose (7200 g), crospovidone (3600 g), magnesium stearate (720 g) and the milled granules (60480 g) were mixed in a tumbler mixer (TM-400S, Showa Chemical Machinery) to give mixed granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained the granules was milled in a powermill grinder (P-7S, Showa Chemical Machinery) using a 1.5 mmφ punching screen to give milled granules. Crystalline cellulose (7200 g), crospovidone (5400 g), magnesium stearate (720 g) and the milled granules (58680 g) were mixed in a tumbler mixer (TM-400S, Showa Chemical Machinery) to give mixed granules B.

(3) The mixed granules A (180 mg) and the mixed granules B (360 mg) were tableted in the form of a bilayer by a rotary tableting machine (AQUA08242L2JI, Kikusui Seisakusho, Ltd.) using a punch (major diameter 14 mm, minor diameter 8 mm) (tableting pressure: 10 kN, weight per tablet: 540 mg) to give core tablets.

(4) Hydroxypropylmethylcellulose (3900 g) and talc (600 g) were dissolved and dispersed in purified water (35000 g) to give dispersion liquid I. Titanium oxide (470 g) and iron oxide (30 g) were dispersed in purified water (10000 g) to give dispersion liquid II. Dispersion liquid II was added to dispersion liquid I, and the mixture was stirred to give a coating dispersion. Using a pan coating machine (DRC-1200, POWREX CORPORATION), the coating dispersion was sprayed on the core tablets obtained in (3) until the weight of the core tablet increased to 20 mg per tablet to give film-coated tablets having the following composition. Then, the film-coated tablets were dried under the reduced pressure at 40° C. for 15 hr.

Composition of Preparation (560 mg)

| | |
|---|---:|
| chlorthalidone | 25 mg |
| mannitol | 111.8 mg |
| crystalline cellulose | 9 mg |
| hydroxypropylcellulose | 5.4 mg |
| crystalline cellulose | 18 mg |
| crospovidone | 9 mg |
| magnesium stearate | 1.8 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 36 mg |
| crospovidone | 27 mg |
| magnesium stearate | 3.6 mg |
| hydroxypropylmethylcellulose | 15.6 mg |
| talc | 2.4 mg |
| titanium oxide | 1.88 mg |
| iron oxide | 0.12 mg |
| total | 560 mg |

Example 13

(1) In a fluid bed granulator (Lab-1, POWREX CORPORATION), compound A (85.36 g), chlorthalidone (100 g), and mannitol (91.26 g) were uniformly mixed and granulated by spraying an aqueous solution of hydroxypropylcellulose (10.8 g), fumaric acid (4 g) and sodium hydroxide (1.38 g), and dried therein. The obtained granules were passed through a 16 mesh sieve (aperture 1.0 mm) to give sieved granules. Croscarmellose sodium (23.46 g), crystalline cellulose (30.6 g), magnesium stearate (3.06 g) and the sieved granules (248.88 g) were mixed in a bag to give mixed granules.

(2) The mixed granules were tableted by a rotary tableting machine (AQUARIUS, Kikusui Seisakusho, Ltd.) using a 6 mmφ punch (tableting pressure: 3 KN/punch, weight per tablet: 90 mg) to give core tablets having the following composition. Then, the core tablets were dried under the reduced pressure at 40° C. for 16 hr.

Composition of Preparation (90 mg)

| | |
|---|---|
| compound A | 21.34 mg |
| chlorthalidone | 25 mg |
| mannitol | 22.815 mg |
| hydroxypropylcellulose | 2.7 mg |
| fumaric acid | 1 mg |
| sodium hydroxide | 0.345 mg |
| croscarmellose sodium | 6.9 mg |
| crystalline cellulose | 9 mg |
| magnesium stearate | 0.9 mg |
| total | 90 mg |

Example 14

In a fluid bed granulator (FD-5S, POWREX CORPORATION), compound A (597.5 g), chlorthalidone (175 g), mannitol (2000 g) and crystalline cellulose (189 g) were uniformly mixed and granulated by spraying an aqueous solution of hydroxypropylcellulose (113.4 g), fumaric acid (28 g) and sodium hydroxide (9.66 g), and dried therein. The obtained granules were passed through a 16 mesh sieve (aperture 1.0 mm) to give sieved granules. Crystalline cellulose (324 g), crospovidone (216 g), magnesium stearate (32.4 g) and the sieved granules (2668 g) were mixed in a tumbler mixer (TM-15, Showa Chemical Machinery) to give mixed granules. The mixed granules were tableted by a rotary tableting machine (VEL50306SS2MZ, Kikusui Seisakusho, Ltd.) using a punch (major diameter 14.8 mm, minor diameter 8 mm) (tableting pressure: 8 KN/punch, weight per tablet: 540 mg) to give core tablets having the following composition. Then, the core tablets were dried under the reduced pressure at 40° C. for 15 hr.

Composition of Preparation (540 mg)

| | |
|---|---|
| chlorthalidone | 25 mg |
| compound A | 85.36 mg |
| mannitol | 285.66 mg |
| crystalline cellulose | 27 mg |
| hydroxypropylcellulose | 16.2 mg |
| fumaric acid | 4 mg |
| sodium hydroxide | 1.38 mg |
| crystalline cellulose | 54 mg |
| crospovidone | 36 mg |
| magnesium stearate | 5.4 mg |
| total | 540 mg |

Example 15

(1) Hydroxypropylcellulose (2800 g) was dissolved in purified water (44070 g) to give liquid I. In a fluid bed granulator (WSG-60, POWREX CORPORATION), chlorthalidone (10750 g), mannitol (48070 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.

(2) Compound A (1024 g), mannitol (2086 g) and crystalline cellulose (216 g) were uniformly mixed in a fluid bed granulator (FD-5S, POWREX CORPORATION) and granulated by spraying an aqueous solution of hydroxypropylcellulose (129.6 g), fumaric acid (48 g) and sodium hydroxide (16.56 g), and dried therein to give granules. The obtained granules were passed through a 16 mesh sieve (aperture 1.0 mm) to give sieved granules B.

(3) Crystalline cellulose (324 g), crospovidone (216 g), magnesium stearate (32.4 g), the milled granules A (907.2 g) and the sieved granules B (1760 g) were mixed in a tumbler mixer (TM-15, Showa Chemical Machinery) to give mixed granules. The mixed granules were tableted by a rotary tableting machine (VEL50306SS2MZ, Kikusui Seisakusho, Ltd.) using a punch (major diameter 14.8 mm, minor diameter 8 mm) (tableting pressure: 8 KN/punch, weight per tablet: 540 mg) to give core tablets having the following composition. Then, the core tablets were dried under the reduced pressure at 40° C. for 15 hr.

Composition of Preparation (540 mg)

| | |
|---|---|
| chlorthalidone | 25 mg |
| mannitol | 111.8 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| hydroxypropylcellulose | 10.8 mg |
| fumaric acid | 4 mg |
| sodium hydroxide | 1.38 mg |
| crystalline cellulose | 54 mg |
| crospovidone | 36 mg |
| magnesium stearate | 5.4 mg |
| total | 540 mg |

Example 16

(1) Hydroxypropylcellulose (2800 g) was dissolved in purified water (44070 g) to give liquid I. In a fluid bed granulator (WSG-60, POWREX CORPORATION), chlorthalidone (2688 g), mannitol (56140 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmφ punching screen to give milled granules B.

(3) Crystalline cellulose (1512 g), crospovidone (882 g), magnesium stearate (151.2 g), the milled granules A (8467 g) and the milled granules B (4108 g) were mixed in a tumbler mixer (TM-60S, Showa Chemical Machinery) to give mixed granules. The mixed granules were tableted by a rotary tableting machine (COLLECT 12K, Kikusui Seisakusho, Ltd.) using a 8.5 mmφ punch (tableting pressure: 6 KN/punch, weight per tablet: 270 mg) to give core tablets.

(4) Hydroxypropylmethylcellulose (390 g) and talc (60 g) were dissolved and dispersed in purified water (3850 g) to give dispersion liquid I. Titanium oxide (47 g) and iron oxide (3 g) were dispersed in purified water (500 g) to give dispersion liquid II. Dispersion liquid II and purified water (150 g) were added to dispersion liquid I, and the mixture was stirred to give a coating dispersion. Using a pan coating machine (DRC-650, POWREX CORPORATION), the coating dispersion was sprayed on the core tablets obtained in (3) until the weight of the core tablet increased to 10 mg per tablet to give film-coated tablets having the following composition. Then, the film-coated tablets were dried under the reduced pressure at 40° C. for 15 hr.

Composition of Preparation (280 mg)

| | |
|---|---:|
| chlorthalidone | 6.25 mg |
| mannitol | 130.55 mg |
| crystalline cellulose | 9 mg |
| hydroxypropylcellulose | 5.4 mg |
| compound A | 21.34 mg |
| mannitol | 43.465 mg |
| crystalline cellulose | 4.5 mg |
| hydroxypropylcellulose | 2.7 mg |
| fumaric acid | 1 mg |
| sodium hydroxide | 0.345 mg |
| crystalline cellulose | 27 mg |
| crospovidone | 15.75 mg |
| magnesium stearate | 2.7 mg |
| hydroxypropylmethylcellulose | 7.8 mg |
| talc | 1.2 mg |
| titanium oxide | 0.94 mg |
| iron oxide | 0.06 mg |
| total | 280 mg |

Example 17

(1) Hydroxypropylcellulose (2800 g) was dissolved in purified water (44070 g) to give liquid I. In a fluid bed granulator (WSG-60, POWREX CORPORATION), chlorthalidone (2688 g), mannitol (56140 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.

(2) Sodium hydroxide (405.8 g) and fumaric acid (1176 g) were dissolved in purified water (38230 g) to give a buffer solution. Hydroxypropylcellulose (3019 g) was dissolved in purified water (47240 g) to give liquid II. In a fluid bed granulator (WSG-60, POWREX CORPORATION), compound A (20060 g), mannitol (40860 g) and crystalline cellulose (4230 g) were uniformly mixed and granulated by spraying the buffer solution (31810 g) and further liquid II (42260 g), and dried to give granules. A part of the obtained granules was milled in a powermill grinder (P-7S, Showa Chemical Machinery) using a 1.5 mmφ punching screen to give milled granules B.

(3) Crystalline cellulose (1512 g), crospovidone (1008 g), magnesium stearate (151.2 g), the milled granules A (4234 g) and the milled granules B (8215 g) were mixed in a tumbler mixer (TM-60S, Showa Chemical Machinery) to give mixed granules. The mixed granules were tableted by a rotary tableting machine (COLLECT 12K, Kikusui Seisakusho, Ltd.) using a punch (major diameter 14 mm, minor diameter 8 mm) (tableting pressure: 10.5 KN/punch, weight per tablet: 540 mg) to give core tablets having the following composition.

(4) Hydroxypropylmethylcellulose (390 g) and talc (60 g) were dissolved and dispersed in purified water (3850 g) to give dispersion liquid I. Titanium oxide (47 g) and iron oxide (3 g) were dispersed in purified water (500 g) to give dispersion liquid II. Dispersion liquid II and purified water (150 g) were added to dispersion liquid I, and the mixture was stirred to give a coating dispersion. Using a pan coating machine (DRC-650, POWREX CORPORATION), the coating dispersion was sprayed on the core tablets obtained in (3) until the weight of the core tablet increased to 20 mg per tablet to give film-coated tablets having the following composition. Then, the film-coated tablets were dried under the reduced pressure at 40° C. for 15 hr.

Composition of Preparation (560 mg)

| | |
|---|---:|
| chlorthalidone | 6.25 mg |
| mannitol | 130.55 mg |
| crystalline cellulose | 9 mg |
| hydroxypropylcellulose | 5.4 mg |
| compound A | 85.36 mg |
| mannitol | 173.86 mg |
| crystalline cellulose | 18 mg |
| sodium hydroxide | 1.38 mg |
| fumaric acid | 4 mg |
| hydroxypropylcellulose | 10.8 mg |
| crystalline cellulose | 54 mg |
| crospovidone | 36 mg |
| magnesium stearate | 5.4 mg |
| hydroxypropylmethylcellulose | 15.6 mg |
| talc | 2.4 mg |
| titanium oxide | 1.88 mg |
| iron oxide | 0.12 mg |
| total | 560 mg |

Reference Example 1

In a fluid bed granulator (Lab-1, POWREX CORPORATION), compound A (42.68 g), lactose (217.32 g), crystalline cellulose (32 g) and monosodium fumarate (10 g) were uniformly mixed, granulated by spraying an aqueous solution of hydroxypropylcellulose (12 g) and monosodium fumarate (10 g), and dried therein to give granules. The obtained granules were passed through a 16 mesh sieve (aperture 1.0 mm) to give sieved granules. The sieved granules (16.2 g) and low-substituted hydroxypropylcellulose (0.8 g) were mixed in a glass bottle to give mixed granules. The mixed granules were tableted by Autograph (manufactured by Shimadzu Corporation, AG-5000B) using a 9.5 mmφ punch (tableting pressure: 7.5 KN/punch, weight per tablet: 398.3 mg) to give core tablets having the following composition. Then, the core tablets were dried under the reduced pressure at 40° C. for 16 hr.

Composition of Preparation (398.3 mg)

| | |
|---|---:|
| compound A | 50 mg |
| lactose | 254.6 mg |
| crystalline cellulose | 37.5 mg |
| hydroxypropylcellulose | 14.1 mg |
| monosodium fumarate | 23.4 mg |
| low-substituted hydroxypropylcellulose | 18.7 mg |
| total | 398.3 mg |

Reference Example 2

In a fluid bed granulator (Lab-1, POWREX CORPORATION), compound A (42.68 g), lactose (217.32 g) and crystalline cellulose (32 g) were uniformly mixed, granulated by spraying an aqueous solution of hydroxypropylcellulose (12 g), and dried therein to give granules. The obtained granules were passed through a 16 mesh sieve (aperture 1.0 mm) to give sieved granules. The sieved granules (15.2 g) and low-substituted hydroxypropylcellulose (0.8 g) were mixed in a glass bottle to give mixed granules. The mixed granules were tableted by Autograph (manufactured by Shimadzu Corporation, AG-5000B) using a 9.5 mmφ punch (tableting pressure: 7.5 KN/punch, weight per tablet: 374.9 mg) to give core tablets having the following composition. Then, the core tablets were dried under the reduced pressure at 40° C. for 16 hr.
Composition of Preparation (374.9 mg)

| | |
|---|---|
| compound A | 50 mg |
| lactose | 254.6 mg |
| crystalline cellulose | 37.5 mg |
| hydroxypropylcellulose | 14.1 mg |
| low-substituted hydroxypropylcellulose | 18.7 mg |
| total | 374.9 mg |

Reference Example 3

In a fluid bed granulator (FD-5S, POWREX CORPORATION), compound A (597.5 g), chlorthalidone (175 g), mannitol (2037 g) and crystalline cellulose (189 g) were uniformly mixed, granulated by spraying an aqueous solution of hydroxypropylcellulose (113.4 g), and dried therein to give granules. The obtained granules were passed through a 16 mesh sieve (aperture 1.0 mm) to give sieved granules. Crystalline cellulose (324 g), crospovidone (216 g), magnesium stearate (32.4 g) and the sieved granules (2668 g) were mixed in a tumbler mixer (TM-15, Showa Chemical Machinery) to give mixed granules. The mixed granules were tableted by a rotary tableting machine (VEL50306SS2MZ, Kikusui Seisakusho, Ltd.) using a punch (major diameter 14.8 mm, minor diameter 8 mm) (tableting pressure: 8 KN/punch, weight per tablet: 540 mg) to give core tablets having the following composition. Then, the core tablets were dried under the reduced pressure at 40° C. for 15 hr.
Composition of Preparation (540 mg)

| | |
|---|---|
| chlorthalidone | 25 mg |
| compound A | 85.36 mg |
| mannitol | 291.04 mg |
| crystalline cellulose | 27 mg |
| hydroxypropylcellulose | 16.2 mg |
| crystalline cellulose | 54 mg |
| crospovidone | 36 mg |
| magnesium stearate | 5.4 mg |
| total | 540 mg |

Reference Example 4

(1) Hydroxypropylcellulose (2800 g) was dissolved in purified water (44070 g) to give liquid I. In a fluid bed granulator (WSG-60, POWREX CORPORATION), chlorthalidone (10750 g), mannitol (48070 g) and crystalline cellulose (3870 g) were uniformly mixed and granulated by spraying liquid I (38870 g), and dried to give granules. A part of the obtained granules was milled in a powermill grinder (P-7S, Showa Chemical Machinery) using a 1.5 mmφ punching screen to give milled granules A.
(2) In a fluid bed granulator (FD-5S, POWREX CORPORATION), compound A (1024 g), mannitol (2151 g) and crystalline cellulose (216 g) were uniformly mixed, granulated by spraying an aqueous solution of hydroxypropylcellulose (129.6 g), and dried therein to give granules. The obtained granules were passed through a 16 mesh sieve (aperture 1.0 mm) to give sieved granules B.

(3) Crystalline cellulose (324 g), crospovidone (216 g), magnesium stearate (32.4 g), the milled granules A (907.2 g) and the sieved granules B (1760 g) were mixed in a tumbler mixer (TM-15, Showa Chemical Machinery) to give mixed granules. The mixed granules were tableted by a rotary tableting machine (VEL50306SS2MZ, Kikusui Seisakusho, Ltd.) using a punch (major diameter 14.8 mm, minor diameter 8 mm) (tableting pressure: 8 KN/punch, weight per tablet: 540 mg) to give core tablets having the following composition. Then, the core tablets were dried under the reduced pressure at 40° C. for 15 hr.
Composition of Preparation (540 mg)

| | |
|---|---|
| chlorthalidone | 25 mg |
| mannitol | 111.8 mg |
| crystalline cellulose | 9 mg |
| hydroxypropylcellulose | 5.4 mg |
| compound A | 85.36 mg |
| mannitol | 179.24 mg |
| crystalline cellulose | 18 mg |
| hydroxypropylcellulose | 10.8 mg |
| crystalline cellulose | 54 mg |
| crospovidone | 36 mg |
| magnesium stearate | 5.4 mg |
| total | 540 mg |

Experimental Example 1

The dried core tablets obtained in Example 1 and Example 13 were stored in a closed glass bottle with a desiccant at 60° C. for 2 weeks. An increase in the amount of decomposed products was measured by the following method.

Compound A was dissolved in an extract at about 1 μg/mL, and the solution was filtered using a non-aqueous filter (0.45 μm) and quantified by high performance liquid column chromatography (HPLC) under the following conditions.

HPLC Conditions detector: ultraviolet absorption photometer, measurement wavelength: 240 nm column: YMC-Pack ProC18, 5 μm, inner diameter: 4.6 mm, length: 150 mm column temperature: 25° C.

mobile phase (A): 0.05 mol/L phosphate buffer (pH 3.0)/acetonitrile mixed solution (9:1)

mobile phase (B): 0.05 mol/L phosphate buffer (pH 3.0)/acetonitrile mixed solution (3:7)

flow: 1 mL/min gradient program (linear)

| time (min) | mobile phase (A) (%) | mobile phase (B) (%) |
|---|---|---|
| 0 (injecting) | 100 | 0 |
| 10 | 70 | 30 |
| 90 | 0 | 100 |
| 91 | 100 | 0 |
| 110 (injecting) | 100 | 0 |

The results are shown in Table 1. As shown in Table 1, by separately granulating each compound, the decomposition of compound A was suppressed.

TABLE 1

| preparation | increase (%) in amount of decomposed products |
|---|---|
| tablet of Example 1 | 2.53 |
| tablet of Example 13 | 6.52 |

Experimental Example 2

The drug dissolution property of the dried core tablets obtained in Example 14 and Reference Example 3 was evaluated by a dissolution test (0.5 w/w % dodecylsodium sulfate-containing phosphate buffer (pH 6.8, 900 mL), Paddle Method, 50 rpm, 37° C.). The results are shown in FIG. 1, wherein $_-\bullet_-$ shows the results of the dried core tablets of Example 14 and $_-\circ_-$ shows the results of the dried core tablets of Reference Example 3.

As shown in FIG. 1, addition of a pH control agent improved the dissolution property.

Experimental Example 3

The dried core tablets obtained in Example 14 and Reference Example 3 were stored in a closed glass bottle with a desiccant at 40° C. for 1 month. An increase in the amount of decomposed products was measured by the following method.

Compound A was dissolved in an extract at about 1 μg/mL, and the solution was filtered using a non-aqueous filter (0.45 μm) and quantified by high performance liquid column chromatography (HPLC) under the following conditions.
HPLC Conditions
detector: ultraviolet absorption spectrophotometer,
measurement wavelength: 240 nm
column: YMC-Pack ProC18, 5 μm, inner diameter: 4.6 mm, length: 150 mm
column temperature: 25° C.
mobile phase (A): 0.05 mol/L phosphate buffer (pH 4.0)/acetonitrile/tetrahydrofuran mixed solution (40:7:3)
mobile phase (B): acetonitrile/0.05 mol/L phosphate buffer (pH 4.0)/tetrahydrofuran mixed solution (49:30:21)
flow: 1 mL/min
gradient program (linear)

| Time (min) | mobile phase (A) (%) | mobile phase (B) (%) |
|---|---|---|
| 0 (injecting) | 100 | 0 |
| 100 | 0 | 100 |
| 101 | 100 | 0 |
| 110 (injecting) | 100 | 0 |

The results are shown in Table 2. As shown in Table 2, addition of a pH control agent suppressed decomposition of compound A.

TABLE 2

| preparation | increase (%) in the amount of decomposed products |
|---|---|
| tablet of Example 14 | 0.51 |
| tablet of Reference Example 3 | 1.80 |

Experimental Example 4

The drug dissolution property of the dried core tablets obtained in Example 15 and Reference Example 4 was evaluated in the same manner as in Experimental Example 2. The results are shown in FIG. 2, wherein $_-\bullet_-$ shows the results of the dried core tablets of Example 15 and $_-\circ_-$ shows the results of the dried core tablets of Reference Example 4.

Figure 2:
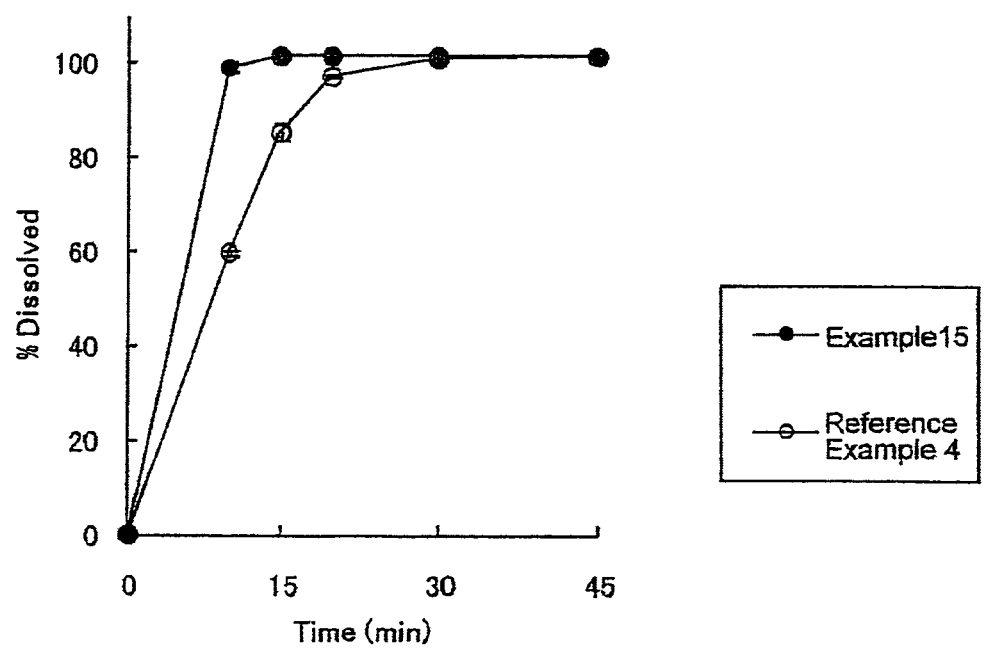
FIG. 2 shows dissolution profiles of the tablets obtained in Example 15 and Reference Example 4.

As shown in FIG. 2, addition of a pH control agent improved the dissolution property.

Experimental Example 5

The dried core tablets obtained in Example 14 and Example 15 were stored in a closed glass bottle with a desiccant at 40° C. for 1 month. An increase in the amount of decomposed products was measured in the same manner as in Experimental Example 3.

The results are shown in Table 3. As show in Table 3, by separately granulating each compound, the decomposition of compound A was suppressed.

TABLE 3

| preparation | increase (%) in the amount of decomposed products |
|---|---|
| tablet of Example 14 | 0.51 |
| tablet of Example 15 | 0.31 |

INDUSTRIAL APPLICABILITY

The solid preparation of the present invention is useful for the prophylaxis or treatment of circulatory diseases such as hypertension, cardiac failure, diabetic nephropathy, arteriosclerosis and the like. The solid preparation of the present invention comprising the aforementioned compound represented by the formula (I), a pH control agent and a diuretic shows superior safety and superior dissolution property of the compound represented by the formula (I) and the diuretic.

While some of the embodiments of the present invention have been described in detail in the above, those of ordinary skill in the art can enter various modifications and changes to the particular embodiments shown without substantially departing from the novel teaching and advantages of the present invention. Such modifications and changes are encompassed in the spirit and scope of the present invention as set forth in the appended claims.

The invention claimed is:

1. A solid preparation comprising
   a first part comprising a compound which is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and a pH control agent and
   a second part comprising chlorthalidone, which is obtained by granulating separately from the first part,
   wherein a pH of a solution or suspension obtained by dissolving or suspending the pH control agent in water at 25° C. at a concentration of 1 w/v % is 2 to 5.

2. The solid preparation of claim 1, wherein the pH control agent is an acidic substance selected from the group consisting of tartaric acid, citric acid, lactic acid, fumaric acid, succinic acid, phosphoric acid, malic acid, ascorbic acid, acetic acid and acidic amino acid, or a salt thereof, or a solvate thereof.

3. The solid preparation of claim 1, wherein the pH control agent is monosodium fumarate, or a combination of fumaric acid and sodium ion donor.

4. The solid preparation of claim 1, which is a single layer tablet obtained by mixing the first part and the second part to give a mixture, and compressing the mixture.

5. The solid preparation of claim 1, which is a multi-layer tablet comprising a first layer comprised of the first part and a second layer comprised of the second part.

6. The solid preparation of claim 1, wherein the pH control agent is in a proportion of 0.01-20 wt % of the preparation.

7. A method of stabilizing a compound which is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt and chlorthalidone in a solid preparation, which method comprises separately granulating a first part comprising the compound and a pH control agent and a second part comprising chlorthalidone to give the solid preparation comprising the first part and the second part, wherein a pH of a solution or suspension obtained by dissolving or suspending the pH control agent in water at 25° C. at a concentration of 1 w/v % is 2 to 5.

8. A method of improving dissolution property of a compound which is (5-methyl-2-oxo-1,3-dioxol-4-yl)methyl 2-ethoxy-1-{[2'-(5-oxo-4,5-dihydro-1,2,4-oxadiazol-3-yl)biphenyl-4-yl]methyl}-1H-benzimidazole-7-carboxylate potassium salt from a solid preparation comprising the compound and chlorthalidone, which method comprises separately granulating a first part comprising the compound and a pH control agent and a second part comprising chlorthalidone to give the solid preparation comprising the first part and the second part, wherein a pH of a solution or suspension obtained by dissolving or suspending the pH control agent in water at 25° C. at a concentration of 1 w/v % is 2 to 5.

* * * * *